United States Patent [19]

Imada et al.

[11] 4,255,344

[45] Mar. 10, 1981

[54] 9-α-HYDROXY STEROIDS

[75] Inventors: Yukio Imada, Yokohama; Sumiko Mizuno, Tokyo, both of Japan

[73] Assignee: Mitsubishi Chemical Industries, Limited, Tokyo, Japan

[21] Appl. No.: 85,639

[22] Filed: Oct. 17, 1979

[30] Foreign Application Priority Data

Nov. 8, 1978 [JP] Japan ................................ 53-137443
Jul. 2, 1979 [JP] Japan ................................ 54-83628

[51] Int. Cl.³ .............................................. C07J 9/00
[52] U.S. Cl. ................................................ 260/397.1
[58] Field of Search ................................... 260/397.1

[56] References Cited

U.S. PATENT DOCUMENTS 4,062,880  12/1977  Antosz et al. ..................... 260/397.1

*Primary Examiner*—Elbert L. Roberts
*Attorney, Agent, or Firm*—Oblon, Fisher, Spivak, McClelland & Maier

[57] ABSTRACT

9α-hydroxy-3-oxopregna-4,17(20)-diene-20-carboxylic acid and its methyl ester, and methods of microbiological production thereof, one comprising cultivating a Rhodococcus species in the presence of the corresponding 3-oxopregna-4,17(20)-diene-20-carboxylic acid or its methyl ester, and the other comprising cultivating Mycobacterium species NRRL B-8054 and a Rhodococcus species in the presence of a sterol substrate.

1 Claim, No Drawings

1

9-α-HYDROXY STEROIDS

BACKGROUND OF THE INVENTION

Field of the Invention

This invention relates to novel compounds, 9α-hydroxy-3-oxopregna-4,17(20)-diene-20-carboxylic acid (hereinafter referred to as "9α-OH-PC") and methyl 9α-hydroxy-3-oxopregna-4,17(20)-diene-20-carboxylate (hereinafter referred to as "9α-OH-PCM") represented by the formula (I):

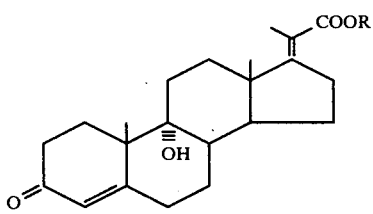

wherein R is hydrogen or methyl, and methods for the microbiological production thereof.

SUMMARY OF THE INVENTION

This invention is directed to novel compounds having the following formula (I):

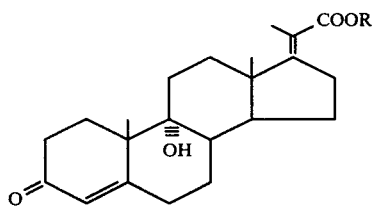

wherein R is hydrogen or methyl, and methods of the microbiological production thereof.

DETAILED DESCRIPTION OF THE PREFERRED EMBODIMENTS

9α-OH-PC and 9α-OH-PCM are very important precursors for the preparation of corticoids. A corticoid having hydroxyl groups at the 11β- and 17α-positions favors the appearance of corticoid activity. Therefore, the compounds of this invention, 9α-OH-PC and 9α-OH-PCM, are valuable as an intermediate since it possesses a hydroxyl group at the 9-position from which the desired 11β-hydroxyl group can be readily introduced by a synthetic process via introduction of a double bond between C-9 and C-11 carbon atoms.

If there is no hydroxyl group at the C-9 position of the B-ring, the 11β-hydroxyl group cannot be introduced without resorting to a microbiological conversion which is said to proceed only at low substrate concentrations, resulting in poor efficiency. A 9α-hydroxy-substituted steroid is also useful as a starting material for the synthesis of a highly active corticoid having a substituent such as fluorine atom at the 9α-position. On the other hand, the presence of a double bond between the C-17 and C-20 carbon atoms in the present compounds makes it possible to readily introduce 17α-hydroxyl group by an organic synthetic process. The 17α-hydroxyl group is normally difficult to introduce.

In addition, the compounds of this invention have a double bond between the C-4 and C-5 carbon atoms in the A-ring. This is another advantageous aspect of this invention, since corticoids usually have such C-4-C-5 double bond.

Many corticoids are diene-type compounds whose A-rings contain a double bond between the C-1 and C-2 carbon atoms in addition to the C-4-C-5 double bond. However, if such diene structure is present in a corticoid precursor, the presence of the C-1-C-2 double bond may interfere with subsequent steps of introduction of 11β- and/or 17α-hydroxyl group. Accordingly, it is preferred that the A-ring of a corticoid precursor or intermediate have a monoene structure as in the compounds of this invention.

The compound, 9α-OH-PC or 9α-OH-PCM, is a steroid having 22 carbon atoms, but it can readily be converted into various corticoids having a basic skeleton of 21 carbon atoms via an appropriate step such as decarboxylation.

From the above discussion, it would be evident to those skilled in the art that the novel compounds of this invention are wholly satisfactory as a corticoid precursor.

The compounds of this invention can be converted into hydrocortisone acetate, one of the typical corticoids, by various organic synthesis routes, an example of which is as follows:

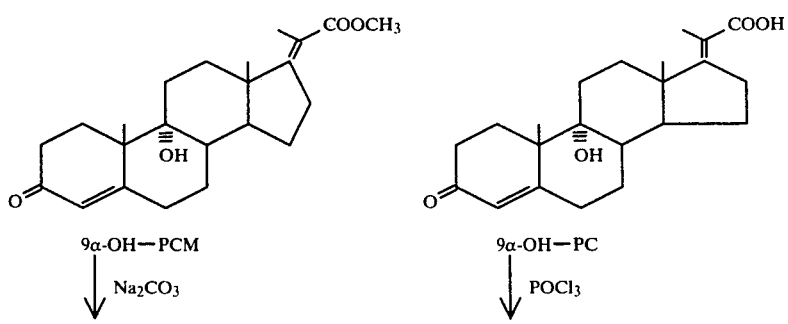

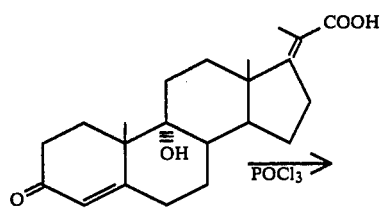

-continued

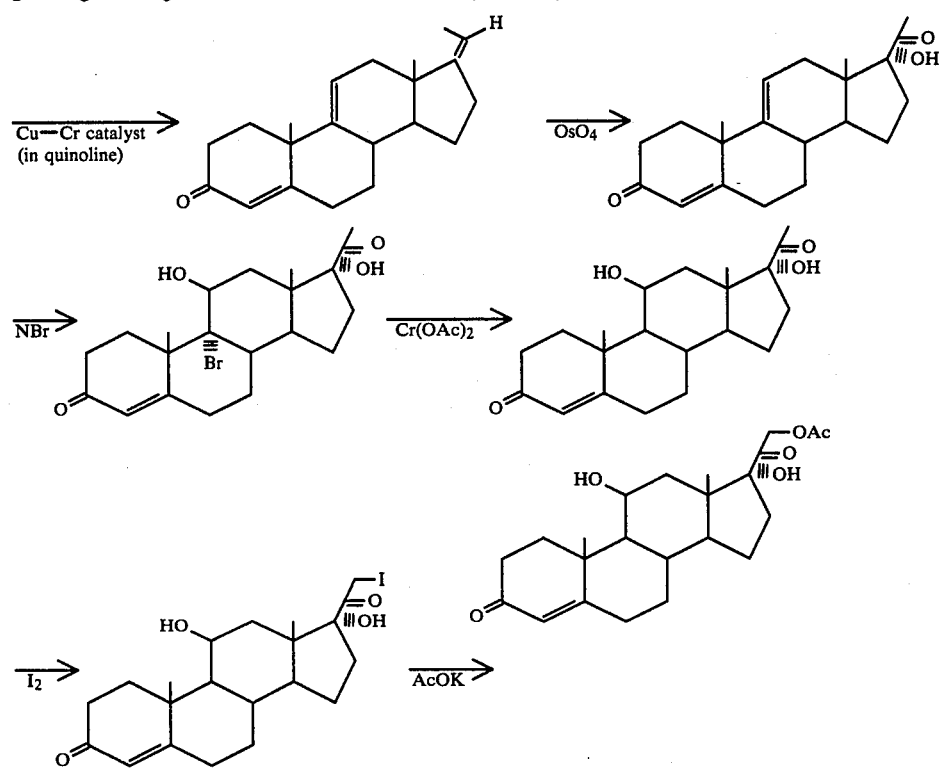

In the above chart, "NBr" represents N-bromosuccinimide and "Ac" represents acetyl group.

When it is desired to further convert the final product, hydrocortisone acetate into prednisolone, the hydrocortisone acetate can be dehydrogenated using a microorganism such as *Arthrobacter simplex* to introduce a double bond between the C-1 and C-2 carbon atoms.

In one aspect of this invention, there is provided a method for the microbiological production of 9α-OH-PC or 9α-OH-PCM which comprises cultivating a *Rhodococcus* species in the presence of the corresponding 3-oxopregna-4,17(20)-diene-20-carboxylic acid (hereinafter referred to as PC) or methyl 3-oxopregna-4,17(20)-diene-20-carboxylate (hereinafter referred to as PCM), as a substrate to introduce a hydroxyl group at the 9-position of the PC or PCM. Another method for the production of 9α-OH-PC or 9α-OH-PCM comprises mixed cultivation or two-step cultivation of *Mycobacterium* species NRRL B-8054 and a *Rhodococcus* species (hereinafter referred to as "R." when abbreviated) in the presence of a sterol as a substrate.

In the method of producing 9α-OH-PC or 9α-OH-PCM from the corresponding PC or PCM, any microorganism capable of introducing a hydroxyl group to PC or PCM at the 9α-position may be used. Exemplary of such microorganisms of choice are the *Rhodococci*. More specifically, those belonging to *Rhodococcus equi* are used to advantage. Known strains of *Rhodococcus equi* are ATCC Nos. 6939, 7698, 7699, 10146, 21107, 21280, 21329, 21521 (subspecies mucilaginosus) and 21690 and IAM 1038. Among these, ATCC 21329 and ATCC 21521 are preferred.

The name *R. equi* has been regarded as *Corynebacterium equi* (hereinafter referred to as "*C.*" equi when abbreviated) so far. The background and history of the change of name from *C. equi* to *R. equi* are described below.

First, M. Tsukamura described a group of mycobacteria which is characterized by a weak acid-fastness and no arylsulfatase activity (at 2 weeks), and also by the ability to utilize sucrose as the sole source of carbon, but the inability to grow no trimethylene diamine as a simultaneous carbon and nitrogen source. They could be differenciated from the species of the genera Mycobacterium (hereinafter referred to as "M." when abbreviated) and Nocardia (hereinafter referred to as "N." when abbreviated).

Tsukamura (J. Gen. Microbiol., 68, 15-26. 1971.) proposed a new genus Gordona (hereinafter referred to as "G." when abbreviated) to accomodate them, showing characters intermediate between the genera Mycobacterium and Nocardia, but rather more closely related to Nocardia. The three species were included in the genus Gordona: i.e., *G. bronchialis* (Tsukamura #3,410=ATCC 25,592=NCTC 10,667, as type strain),

*G. rubra* (Tsukamura #3,605=ATCC 25,593=NCTC 10,668, as type strain) and *G. terrae* (Tsukamura #3,612=ATCC 25,594=NCTC 10,669, as type strain). *G. bronchialis* was typified as type species. *G. rubra* was subsequently considered to be identical to *G. rubropertincta* by M. Tsukamura (Japan, J. Microbiol., 17, No. 3, 189–197. 1973.) and the latter was given priority.

In the next year, M. Tsukamura (Japan, J. Microbiol., 18, No. 1, 37–44. 1974.) described most of the mycobacteria in the 'Rhodochrous' group, which had been named so far, as *M. rhodochrous*, etc., should be included in the genus Gordona by means of the numerical taxonomy. Tsukamura mentioned that some 'rhodochrous' strains should also be classified in Gordona and that proposed three new species: *G. aurantiaca, G. rhodochroa* and *G. rosea*. Tsukamura suggested: *G. rhodochroa*, the species newly defined, contained strain ATCC 13808 carrying the label *Rhodococcus rhodochrous* Zopf (Ber. Dtsch. Botan. Ges., 9, 22–28. 1891.); the appropriate name for the genus appears to be Rhodococcus, and this is the oldest and legitimate generic name under the Bacteriological Code; therefore, Rhodococcus has priority, not his genus Gordona, On the other hand, Goodfellow et al. (J. Gen. Microbiol., 100, 99–122. 1977.) confirmed the establishment of a new genus, destinguishing from the genera Mycobacterium and Nocardia, and gave it the generic name Rhodococcus. This is the same story which was appeared in M. Tsukamura's paper mentioned above.- They examined strains of mycobacteria and nocardiae, and proposed that most strains, which had been included in the genera Mycobacterium or Nocardia so far, should be included in Rhodococcus. They made emendation on the genus Rhodococcus and accomodate nine species: i.e., *R. rhodochrous, R. bronchialis, R. corallinus, R. rhodnii*, R. rubrus, R. rubropertinctus and *R. terrae*. *Corynebacterium equi* was transferred to the genus Rhodococcus as *R. equi* (Magnusson) Goodfellow et Anderson and ATCC 25,729 was designated as type strain. ATCC 25,729, derived from NCTC 1,621, was described as reference strain in the description of *C. equi* in "Bergey's Manual of Determinative Bacteriology, the eighth edition" (however, no type strain was designated there). Meanwhile, the validity to establish a new genus, distinguishing from the genera Mycobacteria and Nocardia, has been accepted by three most authoritative groups on mycobacterial taxonomy, e.g., Lind, Mordarska and Pattyn.

We suppose that the most authoritative paper on the taxonomy of the 'rhodochrous' taxon is that of Goodfellow et al. (l.c. 1977). Therefore, it is most reasonable that the name *R. equi* should be chosen against *C. equi* based upon the taxonomic classification by Goodfellow et al. The characterization of this taxon cited above is fully described in the paper provided by Tsukamura (l.c. 1977), Tsukamura (International Journal of Systematic Bacteriology., 25, 377–382, 1975) and Goodfellow et al. (l.c. 1977).

Either growing cells or resting cells of these bacteria are used in the conversion reaction (i.e., 9α-hydroxylation) of PC or PCM into the corresponding 9α-OH-PC or 9α-OH-PCM. In case resting cells are used, they are grown in an insoluble matter-free medium, then collected by an appropriate means such as centrifugation and resuspended in a buffer solution, an isotonic sodium chloride solution or water which contains the substrate. The suspension is then incubated so as to effect the conversion reaction. During the reaction, agitation and in some cases aeration are necessary.

In case growing cells are used, a medium containing a carbon source and a nitrogen source inorganic salts and, if necessary, nutrients such as vitamines is sterilized, then inoculated with a Rhodococcus species and incubated under shaking or under aeration and agitation. The medium that can be used are described below.

Carbon sources, nitrogen sources and inorganic substances are incorporated in the culture medium.

Examples of such carbon sources are hydrocarbons such as n-paraffins, α-olefins and xylene; alcohols such as methanol, ethanol, glycerol and higher alcohols; organic acids such as succinic acid, acetic acid and higher fatty acids and their salts; saccharides such as starch, maltose, sucrose, glucose and rhamnose; and oils and fats such as linseed oil, soybean oil, sesame oil, corn oil, rapeseed oil, palm oil, fish oil and beef tallow and other tallows.

Examples of natural nutrient sources which contain carbon and nitrogen sources and other nutrient substances are vegetable oil meals such as linseed oil meal, defatted soybean oil meal, cottonseed oil meal and rapeseed oil meal; molasses including hightest molasses, refinery molasses and xylose molasses; bagasse, corn cob, alfalfa, corn steep liquor, distiller's solubles, mieki (an aqueous solution of amino acids mixture prepared by the hydrolysis of soybean oil meal with HCl), fish meal, bran, meat extract, yeast, yeast extract, potato extract, malt extract, gluten, peptone, glutamates, asparagine, glycine, casein, casein hydrolysate and skimmed milk.

Examples of the suitable inorganic substances which are incorporated into the culture medium are nitrogen sources such as ammonium sulfate, ammonium chloride and the like; potassium and phosphorus sources such as dipotassium hydrogen phosphate; salts of such metals as iron, copper, magnesium, manganese, cobalt, zinc, calcium and the like; and ashes of natural products such as molasses.

Other components, e.g., vitamins, can be present in the culture medium if they do not impede the function of the main components.

The composition of the culture medium depends on the microorganism which is used. Carbon sources, nitrogen sources, potassium, phosphorus and magnesium are critical as components in the culture medium.

An anti-foaming agent, e.g., polyoxyalkylene glycol, may be incorporated in the culture medium, if necessary. However, it need not always be added.

The culture medium can contain a surface active agent. This is not required, but does normally render the culture medium more conductive to manipulation. Examples of the suitable surface active agents are nonionic and anion surface active agents such as polyoxyethylene sorbitan monostearate, sorbitan monopalmitate and polyethylene glycol monostearate.

Irrespective of which of growing cells and resting cells are used, the incubation temperature is in the range of 20° to 40° C. The preferred incubation temperature is about in the range of 28° to 37° C.

The medium or the reaction mixture are usually adjusted to pH 5 to 10, preferably pH 6 to 9.

Since the rate of the conversion reaction is low at low cell levels, the cells of Rhodococci are preferably adjusted or grown to a concentration of at least $1 \times 10^9$ cells/ml, preferably at least $1 \times 10^{10}$ cells/ml.

In general, the starting material, PC or PCM, is sterilized with the culture medium. It can also be added to the culture medium after the start of incubation. In addition, it can be added in portions.

The substrate, PC or PCM, after sterilization by dry heat or wet heat, is added in any suitable manner, such as in the form of a powder or a solution in a suitable solvent, e.g., dimethylformamide, methanol, or in the form of a suspension prepared by ultrasonically dispersing it.

It is preferred that PC or PCM, and the surface active agent be simultaneously added because of the increased emulsification of PC or PCM.

While the time required for the conversion varies with various parameters such as concentration of bacterium, temperature and pH, it is preferred to terminate the reaction generally within 7 days, and in some cases in a more brief period of 1 or 2 days. After the lapse of an excessively long period of time, the formed 9α-OH-PC or 9α-OH-PCM usually undergoes degradation so that its amount is gradually decreased. In order to avoid such undesirable results, it is necessary that the amount of 9α-OH-PC or 9α-OH-PCM formed be monitored with the lapse of time and once the amount of the product shows a tendency to decrease the reaction should be terminated by any suitable means such as heat sterilization, addition of an acid or alkali or addition of an organic solvent.

Since the enzyme catalyzing the conversion of PC or PCM into the corresponding 9α-OH-PC or 9α-OH-PCM, namely, 9α-hydroxylating enzyme is generally considered as an induced enzyme, a small amount of PC or PCM is preferably added to the medium during the seed culture of the Rhodococcus species so as to previously induce the enzyme.

Upon completion of the conversion reaction, the 9α-OH-PC or 9α-OH-PCM formed in the culture can be collected, isolated and purified by conventional methods. For example, the fermentation broth is acidified with a mineral acid such as sulfuric acid and then extracted with one to several volumes of a water-immiscible organic solvent, e.g., chloroform or ethyl acetate. The organic solvent is then removed from the extract by distillation and the residual crude 9α-OH-PC or 9α-OH-PCM can be separated from the substrate (PC or PCM), degradation products of 9α-OH-PC or 9α-OH-PCM and other by-products by means of column chromatography on a suitable adsorbent such as a porous resin, silica gel or alumina using an eluent selected from, for example, petroleum ether, benzene, chloroform, ether, acetone, ethanol, methanol and ethyl acetate.

Alternatively, if the crude product predominantly comprises 9α-OH-PC or 9α-OH-PCM, pure crystals of 9α-OH-PC or 9α-OH-PCM are obtained by repeated recrystallization from methanol, ethyl acetate, acetone or the like without resorting to column chromatography.

The substrate, PC or PCM, used in the process according to the invention is usually produced with the aid of a microorganism using a sterol as a substrate and isolated from the resulting culture. Alternatively PC or PCM may be prepared through organic synthetic reactions from an intermediate, e.g., androst-4-ene-3,17-dione (hereinafter referred to as 4AD) which is produced by a microbiological process. The PC or PCM is usually added to the medium prior to inoculation of the *Rhodococcus* species and sterilized together with the medium. However, the PC or PCM may be added in the course of cultivation process in the form of dry heat sterilized powder or steam sterilized suspension in water or in solution dissolved in an appropriate solvent such as methanol.

In accordance with another embodiment of the process of this invention, the compound of this invention, 9α-OH-PC or 9α-OH-PCM is obtained by producing PC or PCM from a sterol with the aid of a PC or PCM-producing microorganism and then inoculating the resulting culture with a Rhodococcus species to produce 9α-OH-PC or 9α-OH-PCM in the medium, as described below in more detail.

The microorganism used for the production of PC from a sterol may be any known PC or PCM-producing microorganism. An example of such microorganisms known so far is Mycobacterium species NRRL B-8054. The production of PC with the aid of Mycobacterium species NRRL B-8054 is described in detail in U.S. Pat. Nos. 3,994,933 and 4,032,408.

Both of PC and PCM are produced by cultivating Mycobacterium species NRRL B-8054, but usually, the amount of PCM produced is larger than that of PC.

Sterols possess a hydroxy group at C-3, normally a double bond at C-5, a side chain of 8 to 10 carbon atoms at C-17, and in some cases, a double bond at C-7, C-8, C-9 (11) or the like of the perhydrocyclopentanophenanthrene nucleus. Examples of such sterols are cholesterol, stigmasterol, campesterol, β-sitosterol, ergosterol, brassicasterol, fucosterol, lanosterol, agnosterol, dihydrolanosterol, dihydroagnosterol, α-sitosterol and the like. Especially preferred are cholesterol, campesterol, stigmasterol and β-sitosterol.

Sterols-containing natural products and processed materials, such as waste oil obtained in purifying fish oil or cuttlefish oil by washing it with alkali, deodorized scum and sludge of vegetable oils, and tall oil can also be used as the starting materials for the process of this invention.

Intermediates in the oxidation of sterols, their C-3 ester derivatives or their C-3 ether derivatives can be used as the starting materials for the process of this invention. The oxidation intermediates include 4-en-3-one derivatives of sterols such as, for example, cholest-4-en-3-one, stigmasta-4,22-dien-3-one and cholesta-4,22-dien-3-one, 3β-hydroxy-22,23-bisnorchor-5-en-22-oic acid and 3β-hydroxy-22,23-bisnorchor-4-en-3-one-22-oic acid.

It is preferred that during the first-step PC and PCM-producing process the cultivation is carried out under optimum conditions for the PC or PCM-producing microorganism and that after the inoculation of a Rhodococcus species, the cultivation is carried out under optimum conditions for the Rhodococcus species. Accordingly, if the pH is greatly shifted during the PC or PCM-fermentation process, an acid or alkali may be added concomitantly with inoculation of the Rhodococcus species so as to readjust the pH at or around 7 and this is often preferred.

The inoculation of the Rhodococci is usually done when the first-step fermentation come to an end, rather than when the first-step fermentation just sets in. In many cases, this results eventually in increased yields of the desired 9α-OH-PC or 9α-OH-PCM.

Prior to inoculation of the Rhodococcus species, it is not always necessary to stop the first-step fermentation, for example, by heat treatment. Thus the culture broth may be inoculated with the Rhodococcus species as the first-step fermentation is still proceeding. In this case both the PC-producing microorganism and the Rhodococcus species are grown simultaneously. Even in such mixed-growing conditions, a large amount of 9α-OH-PC or 9α-OH-PCM can be produced.

Thus, either a two-step cultivation process or a mixed-cultivation process is possible for the cultivation of the two different microorganisms.

When the cells of the Rhodococci are inoculated into the first step culture broth, it is usually not necessary to add further medium. However, if the culture broth resulting from the first-step fermentation appears to be nutritively insufficient to grow the Rhodococci satisfactorily, additional medium components such as meat extract, defatted soybean and/or ammonium nitrate which have been sterilized can be added to the fermentation broth before or after the inoculation of the Rhodococci.

While the culture medium used in the first-step fermentation depends on the particular PC or PCM-producing microorganism used, as a rule any medium component previously listed as the medium useful for the Rhodococci can be used.

The culture of the PC-producing microorganism is usually inoculated with about 0.1 to 30%, preferably 1 to 15% of a fermentation broth of the Rhodococcus species based on the fermentation broth of the PC or PCM-producing microorganism.

In accordance with the method of the invention, 9α-OH-PC or 9α-OH-PCM can be produced in high concentrations in a culture medium. Such embodiment of the invention in which two step reactions of from sterols to PC/PCM and from PC/PCM to 9α-OH-PC/9α-OH-PCM are carried out by fermentative processes to advantage makes it possible to produce 9α-OH-PC/9α-OH-PCM from inexpensive sterols at low cost.

Having generally described this invention, a more complete understanding can be obtained by reference to certain examples which are provided herein for purposes of illustration only are not intended to be limiting in any manner.

In the following examples, PC, PCM, 9α-OH-PC, 9α-OH-PCM and other steroids were assayed by means of gas chromatography and liquid chromatography after they had been silylated, and all the percentages are by weight.

EXAMPLE 1

A seed medium (pH 7.0) having the following composition was prepared:
1.0 percent of glucose
0.3 percent of meat extract
1.0 percent of peptone
0.5 percent of sodium chloride, and remainder-water To a 500 ml shaker flask was added 100 ml of the seed medium.

The flask and its contents were sterilized by autoclaving for a period of 20 minutes at a temperature of 120° C. The medium was inoculated with a loopful of *Rhodococcus equi* ATCC 21,329 and the inoculated medium was incubated for a period of 52 hours at a temperature of 30° C. on a reciprocal shaker having a 7-cm stroke at 120 strokes per minute.

To a 500 ml shaker flask was added 50 ml of a main fermentation medium (pH 7.0) having the following composition:
4 percent of cottonseed oil meal
1.5 percent of yeast, 1.5 percent of soybean oil
0.2 percent of NaNO$_3$, 0.1 percent of K$_2$HPO$_4$
0.1 percent of MgSO$_4$.7H$_2$O, and remainder-water The flask and its contents were sterilized by autoclaving for a period of 20 minutes at a temperature of 120° C. The flask was inoculated with 4 ml of the seed culture broth obtained above. The main fermentation was initiated at a temperature of 30° C. on a reciprocal shaker having a 7-cm stroke at 120 strokes per minute. Thirty hours after the beginning of this incubation, 1.0 g of a sterile PC (in powder) was added under sterile conditions and the incubation was further continued. At forty-eight hours after the addition of PC, the incubation was stopped.

The combined fermentation broth was acidified with sulfuric acid and then extracted with 50 ml of chloroform. Gas-chromatographic analysis of the extract showed that it contained 0.75 g of 9α-OH-PC. In order to identify the substance, the extract was concentrated and developed by thin-layer chromatography on silica gel. The portion of the layer corresponding to 9α-OH-PC was scraped up and then eluted with chloroform. Further purification resorting to repeated recrystallization from ethyl acetate and methanol gave about 300 mg of pure crystals.

The substance was obtained as colorless prisms melting at 241°–242° C. (from ethyl acetate), and its infrared adsorption spectrum (KBr disk) had absorption maxima at 3,450 cm$^{-1}$ (OH), 3,300–2,500 cm$^{-1}$ (COOH) and 1,670 cm$^{-1}$ (α,β-unsaturated carboxylic acid). The data of the NMR analysis were as follows:

(1) in DMSO-d$_6$: 0.90 (3H, s, 18-CH$_3$), 1.24 (3H, s, 19—CH$_3$), 1.86 (3H, s, 2113 CH$_3$), 4.54 (1H, broad-s, —OH), 5.62 (1H, s, 4—H) ppm;

(2) in (CDCl$_3$: 0.96 (3H, s, 18-CH$_3$), 1.32 (3H, s, 19-CH$_3$), 1.96 (3H, s, 21-CH$_3$), 5.84 (1H, broad-s, 4-H) ppm;

(3) in C$_6$D$_5$N: 0.98 (3H, s, 18-CH$_3$), 1.27 (3H, s, 19-CH$_3$), 2.22 (3H, broad-s, 21-CH$_3$), 6.00 (1H, broad-s, 4-H) ppm.

The mass spectrum of the substance had its peaks at m/e=358 (M$^+$ molecule ion peak) and 340 (M - H$_2$O, base peak).

When the substance was esterified with diazomethane, the methyl ester thereof was obtained as colorless prisms (from ethyl ether, m.p. 202°–204° C.). The analytical data of the methyl ester were:

IR ($\nu_{max}^{KBr}$): 3,520 (OH), 1,690

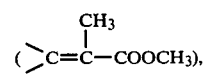

1,660 (—CO—CH=C<) cm$^{-1}$;

NMR (in CDCl$_3$): 0.97 (3H, s, 18-CH$_3$), 1.33 (3H, s, 19-CH$_3$), 1.95 (3H, t, J=~2 Hz, 21-CH$_3$), 3.68 (3H, s, COOCH$_3$), 5.86 (1H, broad-s, 4-H) ppm;

(in C$_6$D$_5$N): 0.93 (3H, s, 18-CH$_3$), 1.26 (3H, s, 19-CH$_3$), 2.02 (3H, t, J=~2 Hz, 21-CH$_3$), 3.67 (3H, s, COOCH$_3$), 6.02 (1H, broad-s, 4-H) ppm.

The methyl ester of 9α-OH-PC is believed to have the following structure:

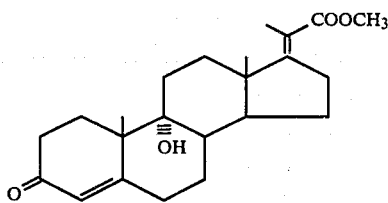

In a 500 ml shaker flask, 50 ml of a main fermentation medium having the same composition as described above except that it contained 1.0 g of PC from the beginning was prepared, then sterilized by autoclaving and inoculated with the same amount of the above-mentioned seed culture broth at the same time as in the above-mentioned experiment. The incubation was carried out under the same conditions without further addition of PC and was stopped after 48 hours. The resulting culture was acidified with the same sulfuric acid and extracted with 50 ml of chloroform. Assay of the 9α-OH-PC content of the extract showed the presence of 0.65 g of 9α-OH-PC in the extract.

EXAMPLE 2

A seed medium (pH 7.0) having the following composition was prepared:
1.0 percent of glucose
0.3 percent of meat extract
1.0 percent of peptone
0.5 percent of yeast extract
0.02 percent of PC, and remainder-water To a 500 ml shaker flask was added 100 ml of the seed medium. The flask and its contents were sterilized by autoclaving for a period of 20 minutes at a temperature of 120° C. The medium was inoculated with a loopful of *Rhodococcus equi* ATCC 21,329 and the inoculated medium was incubated for a period of 48 hours at a temperature of 30° C. on a reciprocal shaker having a 7-cm stroke at 120 strokes per minute.

The combined seed culture broth was cooled and centrifuged to precipitate and harvest the cells. The cells were washed twice with an isotonic sodium chloride solution and then suspended in 25 ml of a phosphate buffer solution (pH 7.5, 1/20 M) containing 1.0% of PC. To a 500 ml shaker flask was added 30 ml of the above suspension. The flask and its contents were incubated under the same conditions as in the seed culture. After the reaction suspension was incubated for 12 hours, it was acidified with sulfuric acid and extracted with 50 ml of chloroform. Assay of the 9α-OH-PC content of the extract showed that about 80 mg of 9α-OH-PC was present in the extract at the end of the 12-hour incubation.

EXAMPLE 3

Seed cultures from *Rhodocuccus equi* ATCC 21,521 were prepared in the same manner as described in Example 1.

To each of two (2) 500 ml shaker flasks was added 50 ml of a main fermentation medium (pH 7.0) having the following composition:
4.0 percent of defatted soybean powder
2.0 percent of yeast
0.25 percent of K₂HPO₄, 0.1 percent of MgSO₄·7H₂O,
0.2 percent of NH₄NO₃
1.0 percent of soybean oil
1.0 percent of PC, and remainder-water The flasks and their contents were sterilized by autoclaving for a period of 20 minutes at a temperature of 120° C. Each of the flask was inoculated with 2 ml of the seed culture broth obtained above. The main fermentation is initiated at a temperature of 30° C. on a reciprocal shaker having 7-cm stroke at 120 strokes per minute. After 35-hour incubation, one of the flasks was removed from the incubuator and the resulting culture was acidified with sulfuric acid and extracted with 50 ml of chloroform. It was confirmed by assay that the extract contained 0.32 g of 9α-OH-PC. The incubation of the other flask was stopped after 59-hour incubation and the combined fermentation broth was likewise acidified with sulfuric acid and extracted with 50 ml of chloroform. Assay of the extract showed that it contained 0.20 g of 9α-OH-PC.

EXAMPLE 4

A seed medium (pH 7.2) having the following composition was prepared:
1.0 percent of glucose
1.0 percent of meat extract
1.0 percent of peptone, and remainder-water To a 500 ml shaker flask was added 100 ml of the seed medium.

The flask and its contents were sterilized by autoclaving for a period of 15 minutes at a temperature of 120° C. The medium was inoculated with a loopful of Mycobacterium species NRRL B-8054 and the inoculated medium was incubated for a period of 72 hours at a temperature of 30° C. on a reciprocal shaker having a 7-cm stroke at 120 strokes per minute.

To each of five (5) 500 ml shaker flasks was added 100 ml of a main fermentation medium (pH 7.0) having the following composition:
4.0 percent of ground soybean
1.0 percent of yeast
0.2 percent of NaNO₃
0.2 percent of K₂HPO₄
0.1 percent of MgSO₄·7H₂O
1.0 percent of cholesterol, and remainder-water The flasks and their contents were sterilized by autoclaving for a period of 20 minutes at a temperature of 120° C. Each of the flasks was inoculated with 2 ml of the seed culture broth obtained above. The main fermentation was initiated at a temperature of 30° C. on a reciprocal shaker having a 7-cm stroke at 120 strokes per minute.

At two hundred and twenty (220) hours after the beginning of the incubation, the medium in each flask was adjusted to around pH 7 under sterile conditions and then inoculated with 8 ml of a seed culture broth of *Rhodococcus equi* ATCC 21,329 prepared in the same way as in Example 1. After this inoculation, the incubation was continued for an additional 48 hours at 30° C. under the same shaking conditions. After the incubation was stopped, the combined fermentation broth was extracted with 2×1.5 l of ethyl acetate. The combined extracts were assayed to determine the steroid contents and it was confirmed by the assay that 0.48 g of 9α-OH-PC was present in the extracts.

EXAMPLE 5

A seed medium (pH 7.2) having the following composition was prepared:
1.0 percent glucose, 1.0 percent meat extract 1.0 percent peptone, and remainder-water To a 500 ml shaker flask was added 100 ml of the seed medium.

The flask and its contents were sterilized by autoclaving for a period of 15 minutes at a temperature of 120° C. The medium was inoculated with Mycobacterium species NRRL B-8054 and the inoculated medium was incubated for a period of 56 hours at a temperature of 30° C. on a reciprocal shaker having a 7-cm stroke at 120 strokes per minute.

To each of two (2) 6 l shaker flasks was added 800 ml of a main fermentation medium (pH 7.0) having the following composition:
4.0 percent of cottonseed oil meal
1.5 percent of yeast
1.0 percent of soybean oil
0.2 percent of NaNO$_3$
0.1 percent of K$_2$HPO$_4$
0.01 percent of MgSO$_4$·7H$_2$O
2.0 percent of cholesterol, and remainder-water The flasks and their contents were sterilized by autoclaving for a period of 20 minutes at a temperature of 120° C. Each of the flasks was inoculated with 20 ml of the seed culture broth obtained above. The main fermentation was initiated at a temperature of 30° C. on a reciprocal shaker having a 7-cm stroke at 100 strokes per minute.

Two hundred and forty (240) hours after the beginning of the incubation, the medium in one of the flasks was adjusted approximately to pH 7 without heat sterilization and simultaneously inoculated with 50 ml of a seed culture broth of Rhodococcus equi ATCC 21,521 prepared in the same manner as in Example 3.

The other flask and its contents were sterilized by autoclaving at 120° C. for 30 minutes. Upon cooling, the medium in the sterilized flask was immediately adjusted to about pH 7 and then inoculated with 50 ml of the same seed culture broth of Rhodococcus equi subsp. mucilaginosus ATCC 21,521. After inoculation of the two flasks, their incubation was resumed at the same time, and stopped 48 hours after the resumption. The resulting fermentation broth in each flask was acidified with sulfuric acid and extracted with 1.6 l of chloroform. The extract derived from the flask which had been heat sterilized prior to the inoculation of Rhodococcus equi was found to contain 0.71 g of 9α-OH-PC. On the other hand, 0.78 g of 9α-OH-PC was formed in the extract obtained without heat sterilization.

EXAMPLE 6

A seed medium (pH 7.2) having the following composition was prepared:
2.0 percent of glycerol
2.0 percent of ground soybean
1.0 percent of yeast extract
0.2 percent of NaNO$_3$
0.1 percent of K$_2$HPO$_4$, and remainder-water To a 500 ml shaker flask was added 100 ml of the seed medium.

The flask and its contents were sterilized by autoclaving for a period of 20 minutes at a temperature of 120° C. The medium was inoculated with a loopful of Mycobacterium species NRRL B-8054 and the inoculated medium was incubated for a period of 68 hours at a temperature of 30° C. on a reciprocal shaker having a 7-cm stroke at 120 strokes per minute.

To each of five (5) 500 ml shaker flasks was added 50 ml of a main fermentation medium having the following composition:
4.0 percent of ground defatted soybean
1.5 percent of yeast
1.0 percent of cottonseed oil meal
0.1 percent of NH$_4$NO$_3$
0.1 percent of MgSO$_4$
0.1 percent of K$_2$HPO$_4$
0.05 percent of Tween-60 (trademark for a non-ionic surface active agent, supplied by Kao Atlas Co.)
2.0 percent various sterols indicated in Table 1 below, and remainder-water Each of the flasks was inoculated with 2 ml of the seed culture broth obtained above. After the inoculation, the flasks and their contents were incubated at 30° C. for 192 hours on a reciprocal shaker having a 7-cm stroke at 120 strokes per minute, and then inoculated each with 4 ml of a seed culture broth of Rhodococcus equi ATCC 21,329 prepared in the same way as in Example 2. Simultaneously with this inoculation, 5 ml of sterile water containing 50 mg of NH$_4$NO$_3$ and 200 mg of yeast extract was added to each flask and the pH in each culture medium was adjusted to about pH 7. Thereafter the incubation was continued for an additional 48 hours before it was stopped. The resulting fermentation broth in each flask was acidified with sulfuric acid and then extracted with 50 ml of chloroform to transfer the steroids into the organic layer. The extracts contained 9α-OH-PC in amounts given in Table 1.

TABLE 1

| Substrate sterol | Yield of 9α-OH—PC (mg) |
| --- | --- |
| Cholesterol | 33 |
| β-Sitosterol (85%) | 20 |
| β-Sitosterol + Campesterol (2 : 1) | 17 |
| Stigmasterol | 5 |
| Cholest-4-en-3-one | 33 |

EXAMPLE 7

Seed cultures from Rhodococcus equi ATCC 21,329 were prepared in the same manner as described in Example 1.

To a 500 ml shaker flask was added 50 ml of the same main fermentation medium as in Example 1 and sterilized in the same manner in Example 1.

The flask was inoculated with 4 ml of the seed culture broth obtained above. The main fermentation was initiated at a temperature of 30° C. on a reciprocal shaker having a 7-cm at 120 strokes per minute. Thirty hours after the beginning of this incubation, 1.0 g of a sterile PCM (in powder) was added under sterile conditions and the incubation was further continued. Forty-eight hours after the addition of PCM, the incubation was stopped. The combined fermentation broth was extracted with 150 ml of ethyl acetate. Gas-chromatographic analysis of the extract showed that it contained 0.50 g of 9α-OH-PCM. In order to identify the substance, the extract was concentrated and developed by thin-layer chromatography on silica gel. The portion of the layer corresponding to 9α-OH-PCM was scraped up and then eluted with ethyl acetate. Further purification resorting to repeated recrystallization from ethyl acetate and ethyl ether gave about 300 mg of pure crystals.

The substance was obtained as colorless prisms melting at 202°–204° C. (from ethyl ether).

In a 500 ml shaker flask, 50 ml of a main fermentation medium having the same composition as described above except that it contained 1.0 g of PCM from the beginning was prepared, then sterilized by autoclaving and inoculated with the same amount of the above-mentioned seed culture broth at the same time as in the above-mentioned experiment. The incubation was carried out under the same conditions without further addition of PCM and was stopped after 48 hours. The resulting culture was extracted with 150 ml of ethyl acetate. Assay of the 9α-OH-PCM content of the extract showed the presence of 0.47 g of 9α-OH-PCM in the extract.

EXAMPLE 8

Example 2 was repeated except that PCM was used as a substrate and the reaction suspension was extracted with 150 ml of ethyl acetate after the incubation for 12 hours. Assay of the 9α-OH-PCM content of the extract showed that about 50 mg of 9α-OH-PCM was present in the extract at the end of the 12-hour incubation.

EXAMPLE 9

Seed cultures from *Rhodococcus equi* subsp. mucilaginosus ATCC 21,521 were prepared in the same manner as described in Example 1.

To a 500 ml shaker flask was added 50 ml of a main fermentation medium (pH 7.0) having the following composition:
4.0 percent of defatted soybean powder
2.0 percent of yeast
0.25 percent of K$_2$HPO$_4$
0.1 percent of MgSO$_4$·7H$_2$O
0.2 percent of NH$_4$NO$_3$
1.0 percent of soybean oil
1.5 percent of PCM, and remainder-water The flask and its contents were sterilized by autoclaving for a period of 20 minutes at a temperature of 120° C. The flask was inoculated with 2 ml of the seed culture broth obtained above. The main fermentation was initiated at a temperature of 30° C. on a reciprocal shaker having 7-cm stroke at 120 strokes per minute.

The incubation was stopped after 59-hour incubation and the combined fermentation broth was extracted with 150 ml of ethyl acetate. Assay of the extract showed that it contained 0.35 g of 9α-OH-PCM.

EXAMPLE 10

Seed cultures from Mycobacterium species NRRL B-8054 were prepared in the same manner as described in Example 4.

To each of five (5) 500 ml shaker flasks was added 100 ml of a main fermentation medium (pH 7.0) having the following composition:
4.0 percent of ground soybean
1.0 percent of yeast
0.2 percent of NaNO$_3$
0.2 percent of K$_2$HPO$_4$
0.1 percent of MgSO$_4$·7H$_2$O
1.5 percent of cholesterol, and remainder-water The flasks and their contents were sterilized by autoclaving for a period of 20 minutes at a temperature of 120° C. Each of the flasks was inoculated with 2 ml of the seed culture broth obtained above. The main fermentation was initiated at a temperature of 30° C. on a reciprocal shaker having a 7-cm stroke at 120 strokes per minute.

Two hundred and twenty (220) hours after the beginning of the incubation, the medium in each flask was adjusted to around pH 7 under sterile conditions and then inoculated with 8 ml of a seed culture of *Rhodococcus equi* ATCC 21,329 prepared in the same way as in Example 1. After this inoculation, the incubation was continued for an additional 48 hours at 30° C. under the same shaking conditions. After the incubation was stopped, the combined fermentation broth was extracted with 2×1.5 l of ethyl acetate. The combined extracts were assayed to determine the steroid contents and it was confirmed by the assay that 0.96 g of 9α-OH-PCM was present in the extracts.

EXAMPLE 11

Example 5 was repeated except that the resulting fermentation broth in each flask was extracted with 1.6 l of ethyl acetate. The extract derived from the flask which had been heat sterilized prior to the inoculation of *Rhodococcus equi* was found to contain 1.67 g of 9α-OH-PCM. On the other hand, 1.60 g of 9α-OH-PC was formed in the extract obtained without heat sterilization.

EXAMPLE 12

Example 6 was repeated except that the resulting fermentation broth in each flask was extracted with 150 ml of ethyl acetate to transfer the steroids into the organic layer. The extracts contained 9α-OH-PCM in amounts given in Table 2 below.

TABLE 2

| Substrate sterol | Yield of 9α-OH—PCM (mg) |
|---|---|
| Cholesterol | 53 |
| β-Sitosterol (85%) | 25 |
| β-Sitosterol + Campesterol (2 : 1) | 30 |
| Stigmasterol | 5 |
| Cholest-4-en-3-one | 28 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A compound, 9α-hydroxy-3-oxopregna-4,17(20)-diene-20-carboxylic acid or its methyl ester which is represented by the formula (I):

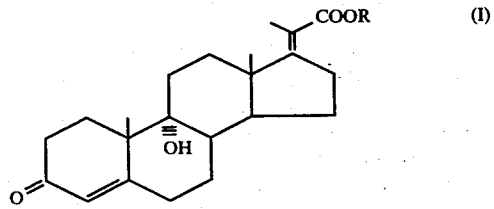

wherein R is hydrogen or methyl.

* * * * *